United States Patent
Latour

(10) Patent No.: US 10,456,275 B2
(45) Date of Patent: *Oct. 29, 2019

(54) ANCHORING SYSTEM FOR PROSTHETIC AND ORTHOTIC DEVICES

(71) Applicant: Shriners Hospital For Children, Tampa, FL (US)

(72) Inventor: Debra Ann Latour, Springfield, MA (US)

(73) Assignee: SHRINERS HOSPITAL FOR CHILDREN, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,416

(22) Filed: Jul. 30, 2014

(65) Prior Publication Data

US 2014/0343693 A1 Nov. 20, 2014

Related U.S. Application Data

(63) Continuation of application No. 13/692,722, filed on Dec. 3, 2012, now Pat. No. 8,821,588, which is a
(Continued)

(51) Int. Cl.
| | |
|---|---|
| A61F 2/78 | (2006.01) |
| A61F 2/54 | (2006.01) |
| A61F 2/58 | (2006.01) |
| A61F 2/68 | (2006.01) |
| A61F 2/60 | (2006.01) |
| A61F 2/50 | (2006.01) |

(52) U.S. Cl.
CPC .......... *A61F 2/78* (2013.01); *A61F 2/54* (2013.01); *A61F 2/588* (2013.01); *A61F 2/60* (2013.01); *A61F 2/68* (2013.01); *A61F 2002/5093* (2013.01); *A61F 2002/7806* (2013.01); *A61F 2002/7862* (2013.01)

(58) Field of Classification Search
CPC ................................. A61F 2/78; A61F 2/80
See application file for complete search history.

(56) References Cited

U.S. PATENT DOCUMENTS

| | | | |
|---|---|---|---|
| 806,598 A | 12/1905 | Stokes | |
| 1,153,334 A * | 9/1915 | Oswald ............... | A41F 1/00 2/335 |

(Continued)

OTHER PUBLICATIONS

U.S. Appl. No. 11/787,161 (US 2007/0250179), filed Apr. 13, 2007 (Oct. 25, 2007) (Abandoned).
(Continued)

*Primary Examiner* — Marcia L Watkins
(74) *Attorney, Agent, or Firm* — Baker Botts L.L.P.

(57) ABSTRACT

Anchoring system including a fastener and a clasp. The fastener includes a substantially planar base, a first clasp-engaging member protruding from a portion of the base and having an outwardly-extending flange, the fastener further including an adhesive suitable to secure the base directly to the skin of a wearer. The clasp includes a first end configured to engage and rotate about the first clasp-engaging member and a second end configured to engage a cable of a prosthetic or orthotic device, the adhesive having a sufficient strength to support manual operation of the prosthetic or orthotic device.

24 Claims, 18 Drawing Sheets

Related U.S. Application Data continuation-in-part of application No. 13/073,248, filed on Mar. 28, 2011, now Pat. No. 8,323,355, which is a continuation of application No. 11/787,161, filed on Apr. 13, 2007, now abandoned.

(60) Provisional application No. 60/798,178, filed on Apr. 19, 2006.

(56) References Cited

U.S. PATENT DOCUMENTS

| | | | |
|---|---|---|---|
| 1,206,753 A | 11/1916 | Desmore | |
| 2,079,426 A * | 5/1937 | Schottenfels | A41C 3/0078 2/311 |
| 2,260,778 A * | 10/1941 | Hodge | A41F 3/02 24/575.1 |
| 2,542,316 A | 2/1951 | Farrar | |
| 2,668,959 A | 2/1954 | Sargeson | |
| 2,686,319 A | 8/1954 | Alderson | |
| 3,295,515 A | 1/1967 | Kahn | |
| 3,868,946 A | 3/1975 | Hurley | |
| 3,911,537 A | 10/1975 | Mazur | |
| 4,011,637 A * | 3/1977 | Mazur | A44B 11/2588 24/598.1 |
| 4,180,870 A | 1/1980 | Radulovic et al. | |
| 4,258,441 A | 3/1981 | Bell | |
| 4,274,420 A * | 6/1981 | Hymes | A61B 5/04087 600/391 |
| 4,291,421 A | 9/1981 | Massey et al. | |
| 4,685,925 A | 8/1987 | Childress et al. | |
| 5,206,957 A | 5/1993 | Gulick | |
| 5,400,782 A | 3/1995 | Beaubiah | |
| 5,651,792 A | 7/1997 | Telikicherla | |
| 5,800,572 A | 9/1998 | Loveall | |
| 5,813,981 A | 9/1998 | Carim | |
| 6,074,420 A * | 6/2000 | Eaton | A61F 2/52 623/7 |
| 6,500,210 B1 * | 12/2002 | Sabolich | A61F 2/583 623/24 |
| 6,719,713 B2 | 4/2004 | Mason | |
| 6,736,855 B2 | 5/2004 | Bertels | |
| 8,323,355 B2 | 12/2012 | Latour et al. | |
| 8,821,588 B2 | 9/2014 | Latour et al. | |
| 2003/0013999 A1 | 1/2003 | Grelsamer | |
| 2003/0073378 A1 * | 4/2003 | Davis | A41C 3/02 450/88 |
| 2003/0093158 A1 | 5/2003 | Phillips et al. | |
| 2004/0138763 A1 | 7/2004 | Perkins et al. | |
| 2005/0277859 A1 | 12/2005 | Carlsmith | |
| 2007/0032884 A1 | 2/2007 | Veatch | |
| 2007/0106187 A1 | 5/2007 | Campbell et al. | |
| 2007/0250179 A1 | 10/2007 | Latour et al. | |

OTHER PUBLICATIONS

U.S. Appl. No. 13/073,248 (U.S. Pat. No. 8,323,355), filed Mar. 28, 2011 (Dec. 4, 2012).
U.S. Appl. No. 13/692,722 (U.S. Pat. No. 8,821,588), filed Dec. 3, 2012 (Sep. 2, 2014).
U.S. Appl. No. 11/787,161, Jun. 8, 2011 Notice of Abandonment.
U.S. Appl. No. 11/787,161, Oct. 26, 2010 Final Office Action.
U.S. Appl. No. 11/787,161, Jan. 27, 2010 Applicant Summary of Interview with Examiner.
U.S. Appl. No. 11/787,161, Dec. 28, 2009 Examiner Interview Summary.
U.S. Appl. No. 13/073,248, Oct. 29, 2012 Issue Fee payment.
U.S. Appl. No. 13/073,248, Jul. 31, 2012 Notice of Allowance.
U.S. Appl. No. 13/073,248, Jun. 18, 2012 Appeal Brief filed.
U.S. Appl. No. 13/073,248, Apr. 24, 2012 Advisory Action.
U.S. Appl. No. 13/073,248, Apr. 11, 2012 Response to Final Office Action.
U.S. Appl. No. 13/073,248, Mar. 16, 2012 Notice of Appeal.
U.S. Appl. No. 13/073,248, Dec. 16, 2011 Final Office Action.
U.S. Appl. No. 13/073,248, Oct. 25, 2011 Response to Non-Final Office Action.
U.S. Appl. No. 13/073,248, May 25, 2011 Non-Final Office Action.
U.S. Appl. No. 13/692,722, May 5, 2014 Issue Fee payment.
U.S. Appl. No. 13/692,722, May 2, 2014 Amendment after Allowance.
U.S. Appl. No. 13/692,722, Feb. 3, 2014 Notice of Allowance.
U.S. Appl. No. 13/692,722, Jan. 2, 2014 Response to Restriction Requirement.
U.S. Appl. No. 13/692,722, Dec. 2, 2013 Restriction Requirement.
Dictionary Definition for "Durable".
Dictionary Definition for "Flange".
Cambridge Online Dictionary, definition "harness", accessed Oct. 20, 2010.
Merriam Webster Online Dictionary, definition "Harness", accessed Oct. 19, 2010.
Brunnstrom, "Shoulder Region", Clinical Kinesiology, 3rd Edition, Chapter 5, F.A. Davis Company, Philadelphia, 1972.
Collier et al., "Axilla bypass ring for shoulder harness for upper-limb prothesis", Journal of Prosthetics and Orthotics, 8(4): 130-131, 1996.
Crandall et al., "Pediatric unilateral below-elbow amputees: retrospective analysis of 34 patients given multiple prosthetic options", J Pediatr Orthop, 22(3): 380-383, 2002.
Curran et al., "The prosthetic treatment of upper limb defiency", Prosthet Orthot Int., 15(2): 82-87, 1997.
Fryet et al., "Upper-limb prosthetics/body-powered components", Atlas of Limb Prosthetics: Surgical, Prothetic, and Rehabilation Principles, Mosby, 2nd Edition, chapter 6A, pp. 107-131, 1992.
Fryet et al., "Upper-limb prosthetics/body-powered components", Atlas of Limb Prosthetics: Surgical, Prothetic, and Rehabilation Principles, Mosby, 2nd Edition, chapter 6B, pp. 133-150, 1992.
Kejlaa, "Consumer concerns and the functional value of protheses to upper limb amputees", prosthet Orthot Int., 17(3): 157-163, 1993.
Krebs et al., "Prosthetic management of children with limb deficiencies", Phys ther., 71(12): 934, 1991.
Krebs et al., "acceptability of the NYU No. 1 child-sized body powered hand", arch Phys Med Rehabil., 69(2): 137-141, 1998.
Kuyper et al., "Prosthetic management of children in the Netherlands with upper limb deficiencies", Prosthet Orthot int., 25(3): 228-234, 2001.
Meeks et al., "evaluation of a new design: Body-powered, upper-limb prosthesis without shoulder harness", Journal of Prosthetics and Orthostics, 1(1): 45-49, 1989.
Pierson, "An overview of skin contact for pressure-sensitive adhesives", Tappi Journal, Jun. 1990.
Postema et al., "Prosthesis rejection in children with a unilateral congenital arm defect", Clin. Rehabil., 13(3): 243-249, 1999.
Roninger, "Study finds chronic pain in fact of life amputess", Biomechanics, 13(1): 15-16, 2006.
Roth-Isigkeit et al., "pain among children and adolescents: Restriction in daily living and triggering factors", Pediatrics, 115(2): 125-162, 2005.
Shaperman et al., "is body powered operation of upper limb protheses feasible for young limb deficient children?", Prosthet. Orthot. Int., 19(3): 165-175, 1995.
International Search Report and Written Opinion dated Dec. 12, 2007 from International Application No. PCT/US07/66862.

* cited by examiner (PIOR ART)

ANCHORING SYSTEM FOR PROSTHETIC AND ORTHOTIC DEVICES

CROSS REFERENCE TO RELATED APPLICATIONS

This application is a continuation of U.S. patent application Ser. No. 13/692,722, filed on Dec. 3, 2012, now U.S. Pat. No. 8,821,558, which is a continuation-in-part of U.S. patent application Ser. No. 13/073,248, filed Mar. 28, 2011, now U.S. Pat. No. 8,323,355, which is a continuation of U.S. patent application Ser. No. 11/787,161, filed Apr. 13, 2007, now abandoned, which claims priority to U.S. Patent Application Ser. No. 60/793,178, filed on Apr. 19, 2006, the entire contents of each of which are incorporated by reference herein, and from each of which priority is claimed

TECHNICAL FIELD

This disclosed subject matter relates to prosthetic and orthotic devices, as well as methods of securing the prosthetic and orthotic devices on a wearer.

BACKGROUND

Various limb prosthesis and orthotic devices have been designed that require a harness system for their operation. However, the benefits of prostheses and orthotic devices are diminished by the harness system in that it can cause user discomfort, reduced cosmesis due to pulling on clothing, and in the case of upper limb prostheses or orthotic devices, poor posturing of the shoulders, shoulder muscle asymmetry, and perceived pain in the contralateral shoulder, arm, and hand due, e.g., to impingement of axillae. Further, the function of a prosthetic or orthotic device with a harness system is often limited in that contralateral body power is needed to operate a terminal device affixed to the prosthetic or orthotic device.

SUMMARY

The present application provides a novel anchoring system that can replace the typical harness system used with cable-activated prosthesis and orthotic systems. Use of the anchoring system with a prosthetic or orthotic device can eliminate many of the problems associated with using a harness system.

Accordingly, in one aspect, the application provides an anchoring system. The anchoring system can include (i) a fastener comprising a base and a clasp-engaging member, the fastener further including an adhesive suitable to secure the base directly to skin of a wearer; and (ii) a clasp, comprising a first end configured to engage and rotate about the clasp-engaging member and a second end configured to engage an cable of a prosthetic or orthotic device.

In another aspect, the application provides a prosthetic or orthotic system. The system can include: (a) an anchoring system that includes (i) a fastener comprising a base and a clasp-engaging member, the fastener further including an adhesive suitable to secure the base directly to skin of a wearer; and (ii) a clasp comprising a first end configured to engage and rotate about the clasp-engaging member and a second end engaged with a cable of a prosthetic or orthotic device; and (b) a prosthetic or orthotic device comprising a cable and a terminal device, wherein the cable comprises a first end operatively coupled to the terminal device and a second end engaged with the second end of the clasp.

The base and clasp engaging member can together be a unitary structure. Alternatively, the clasp engaging member can be detachably connected to the base. The clasp-engaging member can be flange, button, or knob that protrudes from a portion of the base, e.g., from about the center axis of the base.

The base can be a flat member that includes an adhesive side adapted to adhere the base to the body of a wearer of the device, and a non-adhesive side. The base can be any shape, e.g., circular, rectangular, square, or triangular in shape. The base can include a thermoplastic material, e.g., a perforated thermoplastic material. The fastener can also include a thermoplastic material. The clasp can be any functional shape, e.g., a loop or hook structure.

The anchoring system can further include a linker between the clasp and the activation cable, and can be adjustable to accommodate different sizes of wearers, lengths of prosthetic or orthotic devices, and lengths of activation cables. The linker can include a cloth material, such as a canvas strap, or a Dacron webbing.

The prosthetic or orthotic system can include a prosthetic device, such as a lower limb prosthesis, including a prosthetic leg or the like, or an upper limb prosthesis including an above elbow prosthesis, a below elbow forearm prosthesis, a hand prosthesis (prosthetic hand), a partial hand prosthesis (such as M-Fingers™ products made by Partial Hand Solutions, LLC, Massachusetts). The prosthetic device can include a prehensile terminal device, such as a prosthetic hand or hook. Alternatively, the prosthetic or orthotic system can include an orthotic device, such as a lower limb orthotic device including a dynamic leg splint or dynamic ankle foot orthosis, or an upper limb orthotic device including a dynamic hand (such as, SaeboFlex™ made by Saebo, Inc., North Carolina), a dynamic forearm, and a dynamic elbow splint.

In yet another aspect, the application provides a method of securing a prosthetic or orthotic device to a wearer. The method includes providing an anchor comprising (i) a fastener including a base, and a clasp-engaging member, and (ii) a clasp having a first end configured to engage and rotate about the clasp-engaging member, and a second end; adhering the fastener at a predetermined location on the skin of a wearer using an adhesive suitable to secure the base directly to skin of the wearer; coupling the clasp at the second end to a cable of a prosthetic or orthotic device; and engaging the clasp and the clasp-engaging member o secure the prosthetic or orthotic device on the wearer. Although the above procedure is described sequentially, the sequence of the operation can be varied as appropriate for the configuration of the prosthetic or orthotic device, or according to the user's preference. Thus, variations of the sequence of operation are encompassed in the appended claims.

Unless otherwise defined, all technical and scientific terms used herein have the same meaning as commonly understood by one of ordinary skill in the art. Although methods and equipment similar or equivalent to those described herein can be used in the practice of the disclosed subject matter, suitable methods and equipment are described below. All publications and other references mentioned herein are incorporated by reference in their entirety. In case of conflict, the present specification, including definitions, will control. In addition, the materials, methods, and examples are illustrative only and not intended to be limiting.

The details of one or more embodiments of the disclosed subject matter are set forth in the accompanying drawings and the description below. Other features and advantages of the disclosed subject matter will be apparent from the description and drawings, and from the claims.

DETAILED DESCRIPTION

The application provides an anchoring system for cable-activated and/or cable-supported prosthetic and orthotic devices. The new anchoring system enables the user to operate the cable-activated prosthetic or orthotic device's terminal device, e.g., by applying tension to the cable using scapulo-thoracic movement, without the aid of a harness system, and thus avoids the problems associated with such harness systems.

The application also provides a prosthetic or orthotic system that includes the anchoring system, as well as methods for securing such a system to a wearer.

In accordance with one aspect of the disclosed subject matter, a method is provided. The method includes providing an anchor comprising (i) a fastener including a base, and a clasp-engaging member, and (ii) a clasp having a first end configured to engage and rotate about the clasp-engaging member, and a second end; adhering the fastener at a predetermined location on the skin of a wearer using an adhesive suitable to secure the base directly to skin of the wearer; coupling the clasp at the second end to a cable of a prosthetic or orthotic device; and engaging the clasp and the clasp-engaging member to secure the prosthetic or orthotic device on the wearer.

Reference will be now made for purpose of illustration and not limitation to the embodiments of the anchoring system and method as depicted in the figures. The description is an exemplification of the principles of the disclosed subject and is not intended to be limited to the particular embodiments illustrated.

Figure 1:
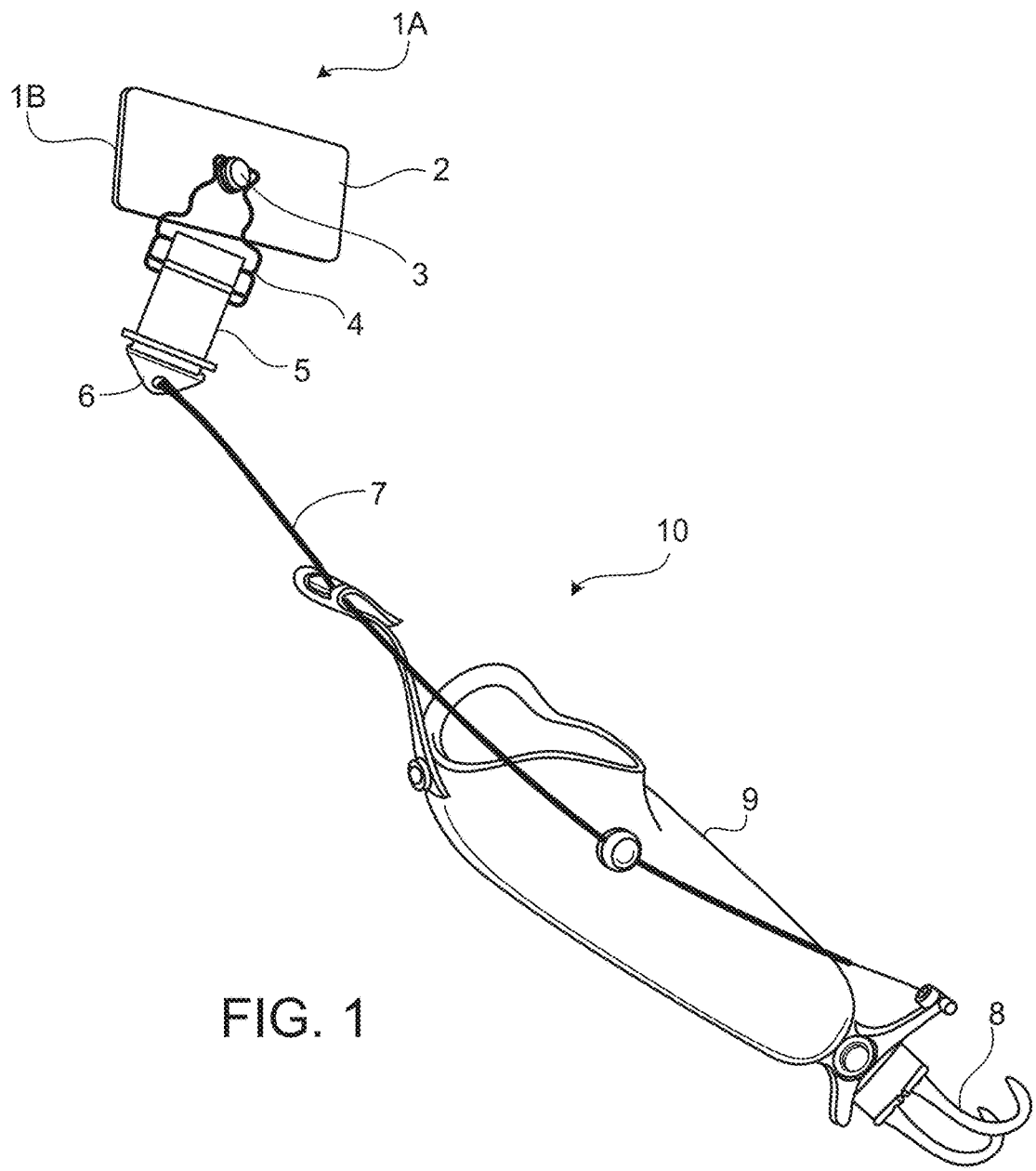
FIG. 1 is a perspective view of a prosthetic device with an exemplary assembled anchoring system.

FIG. 1 provides an overview of an exemplary assembled prosthetic system 10 and an exemplary anchoring system 1A. The anchoring system includes, as its main components, a fastener 1B comprising a base 2 and a clasp-engaging member 3, and a clasp 4. The system optionally includes a linker 5. In FIG. 1, linker 5 is connected to an activation cable 7 through a ball joint 6 between the two, such that the entire anchoring system is pivotably connected to a second end of activation cable 7. Activation cable 7 is connected at a first end to a terminal device 8, in this case a hook, mounted on a prosthetic device 9. In certain embodiments, clasp 4 can be configured to directly engage activation cable 7 of prosthetic or orthotic device 9, and linker 5 can be excluded.

Figure 2:
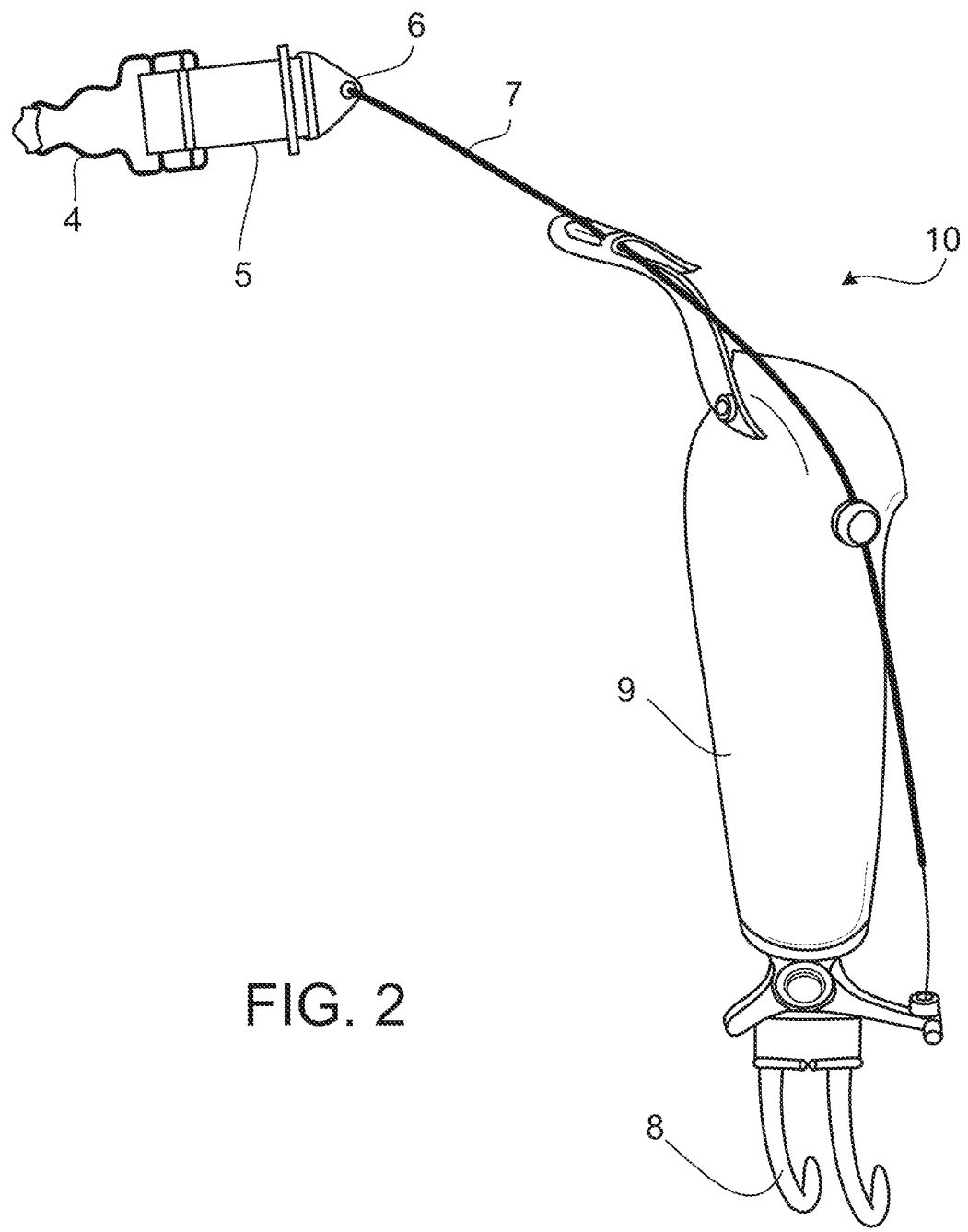
FIG. 2 is a perspective view of the prosthetic device depicted in FIG. 1 in a unassembled state.
Figure 3A:
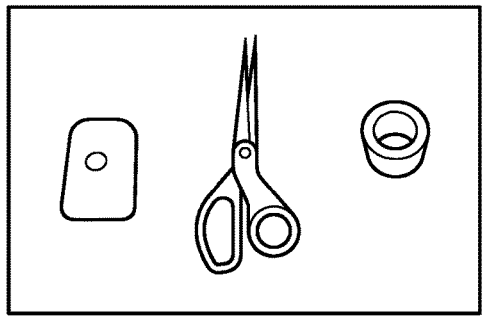
FIGS. 3A-3G illustrate assembly of an exemplary fastener.
Figure 3B:
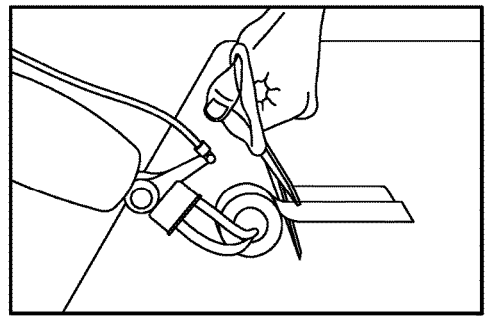
Figure 3C:
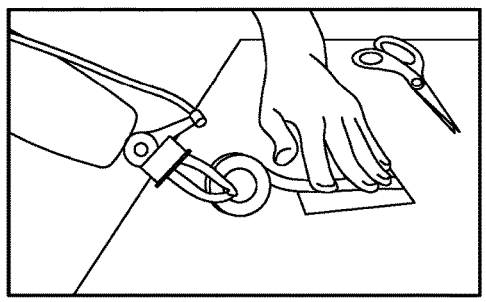
Figure 3D:
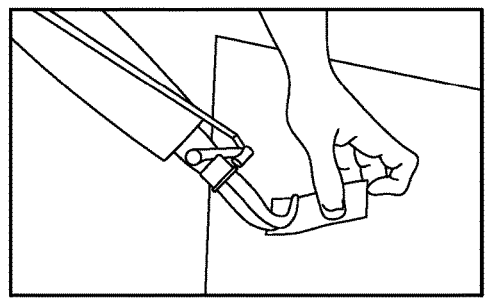
Figure 3E:
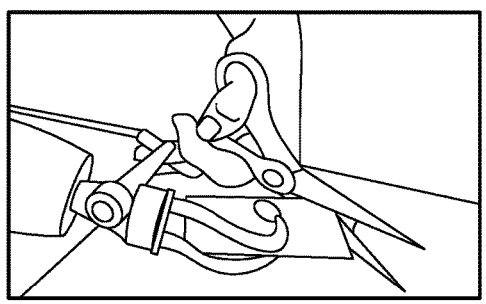
Figure 3F:
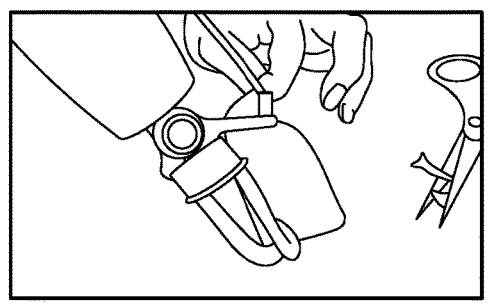
Figure 3G:
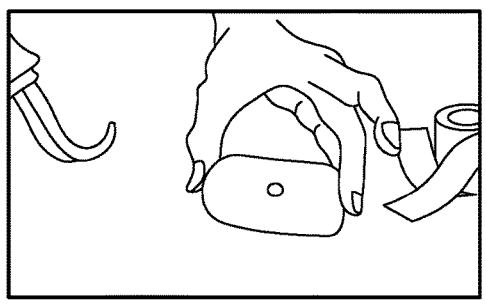

FIG. 2 provides a slightly different perspective of the exemplary system depicted in FIG. 1 in an unassembled state. Clasp 4 is disengaged from clasp engaging member 3, Fastener 1B is not shown in FIG. 2.

Fastener 1B can be a unitary structure, i.e., clasp engaging member 3 and base 2 can be formed as a single unit, and optionally including the same material, e.g., a thermoplastic material. Alternatively, base 2 and clasp engaging member 3 can be formed as separable units. In such embodiments, base 2 and clasp engaging member 3 can include the same or different materials.

Where base 2 and clasp-engaging member 3 are separable units, base 2 and clasp-engaging member 3 can be connected using any method known to those of skill in the art, e.g., riveting or bonding (e.g., gluing). Alternatively or in addition, base 2 can be constructed with a perforation configured such that it can receive clasp-engaging member 3 therethrough and hold clasp-engaging member 3 in position optionally with or without using other means. Base 2 can also be constructed with a perforation to accommodate embodiments wherein clasp-engaging member 3 is separable from base 2 and attached (reversibly or irreversibly) to clasp 4, and wherein the system is assembled by inserting clasp engaging member 3 into a perforation in base 2.

Base 2 can be constructed as a flat sheet of material, e.g., a patch. The flat sheet of material can be formed into any shape and size desirable to a skilled practitioner, including, inter alia, a circle, square, rectangle, triangle or octagon. Base 2 can be a solid sheet of material or have one or more perforations, e.g., to enhance air flow through base 2 to the wearer's skin. As embodied herein, the base is constructed so as to have sufficient strength and durability to support the manual operation of the prosthetic and orthotic device. For example, skilled practitioners will appreciate that it can be made of any material useful in such applications, including but not limited to, a fabric, thermoplastic material, or metal, or a mixture thereof. For example, the base can be made of a perforated thermoplastic material, e.g., AQUAPLAST-T™ (Rolyan®).

Base 2 can include an adhesive on at least one side, which can be used to adhere fastener 1A to the skin of the wearer. The adhesive can be any adhesive known in the art, e.g., an adhesive acceptable for use on a wearer's skin. For example, the adhesive can be a medical glue or a tape (e.g., a double sided tape such as toupee tape) Suitable medical tapes can include pressure sensitive adhesives, much as acrylics. In one example, the adhesive is a TOPSTICK® double-sided tape manufactured by Vapon Inc., New Jersey. The adhesive can be selected to provide sufficient adhesion to support the manual operation of the prosthetic or orthotic device for a desired duration of time (e.g., a day, a few days, or longer).

Clasp-engaging member 3 can be any member that is suitable for use as a connection point between base 2 and clasp 4. In certain embodiments, clasp-engaging member 3 is a button (e.g., a so-called "bachelor button"), knob, or flange. In other embodiments, clasp-engaging member 3 can be a screw fastened on the base. Skilled practitioners will appreciate that clasp-engaging member can be made of any rigid material, e.g., a thermoplastic material or metal, e.g., steel, aluminum or titanium.

In accordance with another aspect of the disclosed subject matter, the anchoring system can include one or more additional clasp-engaging members, wherein each clasp engaging member is provided to support or manually operate a respective cable of a prosthetic or orthotic device. For example, and with reference to FIG. 6, the anchoring system 1A can further include (a) a second clasp-engaging member 3' spaced from the first clasp-engaging member 3, and (b) a second clasp 4' having a first end configured to engage and rotate about the second clasp-engaging member 3'. The second clasp 4' can be coupled to a second linker 5' which can connect to a second cable, e.g., a supporting cable (not shown), of the prosthetic arm 9. Additionally or alternatively, a plurality of individual anchors can be adhered to the skin of the wearer, where each anchor supports or manually operates a respective cable of a prosthetic or orthotic device.

Clasp 4 is depicted in FIG. 1 and FIG. 2 as a typical clothing (e.g., "overalls")-type clasp. However, skilled practitioners will appreciate that many variations on this theme are possible. For example, clasp 4 can he a simple hook or loop structure, configured at one end to connect with clasp-engaging member 3 and at the other end to connect with linker 5 or directly with activation cable 7, such that linker 5 can be excluded. Clasp 4 can be made of any material, e.g., a metal (e.g., steel or titanium) or thermoplastic material. As an example, the clasp can be a Hosmer nylon suspension clasp (Fillauer Company, Chattanooga, Tenn.)

Linker 5 is optionally included in the system and can be any material, e.g., a cloth, such as canvass, metal, or thermoplastic material. Linker 5 can be adjustable in length, e.g., to accommodate, inter alia, different sizes of wearers, lengths of prosthetic or orthotic devices, etc. As an example, the linker can include a TRS clip (TRS, Boulder, Colo.). Depending upon the needs of the prosthetic or orthotic device, as discussed below, the anchor and/or linker 5 can further include an electronic component, such as a linear transducer, for transmitting a myoelectric signal to the patient to control the prosthetic or orthotic device.

Anchoring system 1A can be used with any cable-activated prosthesis or orthotic device. For purpose of illustration and not limitation, although particularly beneficial for body powered prosthetic or orthotic devices, it is recognized the anchor system disclosed herein can also be used for electrochemically operated devices, such as a myoelectric devices or the like. The prosthetic device 9 shown in FIG. 1 and FIG. 2 is a below elbow forearm prosthesis with a modified Muenster socket with a terminal hook. However, skilled practitioners will appreciate that many other cable-activated and/or supported prosthetic and orthotic devices for upper and lower limbs are known and commercially available, as are other terminal devices. For example, and with reference to the figures, anchoring system 1A can be used with an upper limb prosthesis such as an above elbow prosthesis 91 (illustrated in FIG. 6), a below elbow prosthesis 92 (illustrated in FIG. 7), a hand prosthesis (prosthetic hand), or a partial hand prosthesis 93 (illustrated in FIG. 8), or other prehensile device. As another example, with regard to orthotic devices, anchoring system 1A can be used with an upper limb orthotic device 94 as illustrated in FIG. 9, such as a dynamic splint, e.g., a dynamic hand, a dynamic forearm, or a dynamic elbow splint.

With reference to FIGS. 5A-5C and FIGS. 6-9, which depict various uses of the anchoring system of the disclosed subject matter with an upper limb prosthetic or orthotic device, the anchoring system 1A can be placed ipsilaterally with respect to the prosthesis or the orthosis. For example, and as depicted herein, the anchoring system 1A can be placed between the scapula and the spine, and medial to the scapula of the wearer. For another example (not shown) the anchoring system 1A can be positioned slightly higher in the scapulo-vertebral area, with the clasp-engaging member being proximate the top of the anchoring system. The clasp-engaging member can be coupled to an activation cable of an upper limb prosthesis or orthosis, such as a prosthetic elbow, through a clasp (e.g., a nylon suspension clip) and a linker (e.g., a Dacron webbing). For this configuration, a shoulder shrug can activate the movement of the prosthetic or orthotic device.

Figure 6A:
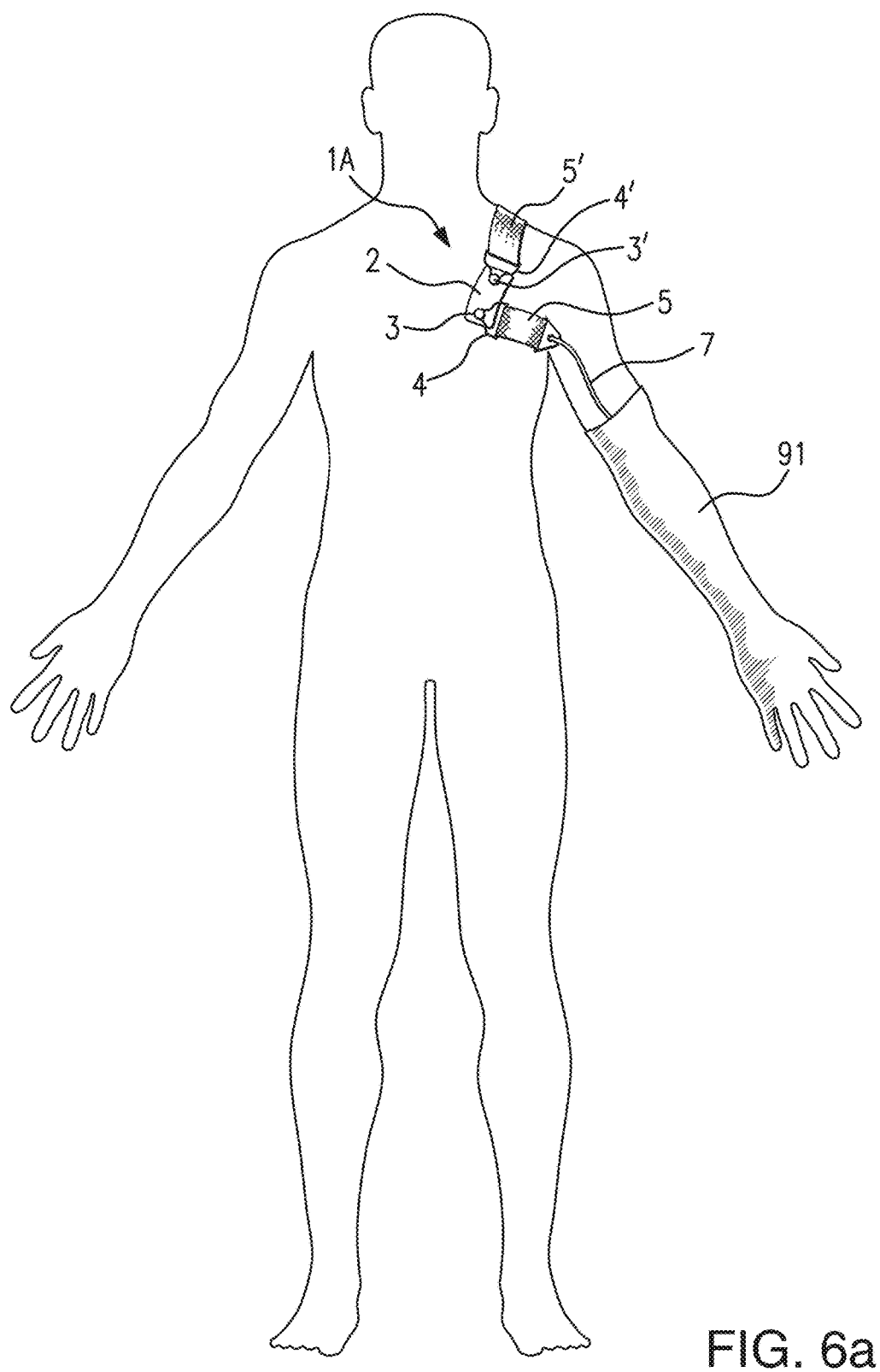
FIG. 6a is a posterior schematic view of a wearer of an above elbow prosthetic arm used in conjunction with an exemplary anchoring system having two clasp-engaging members according to the disclosed subject matter.
Figure 7:
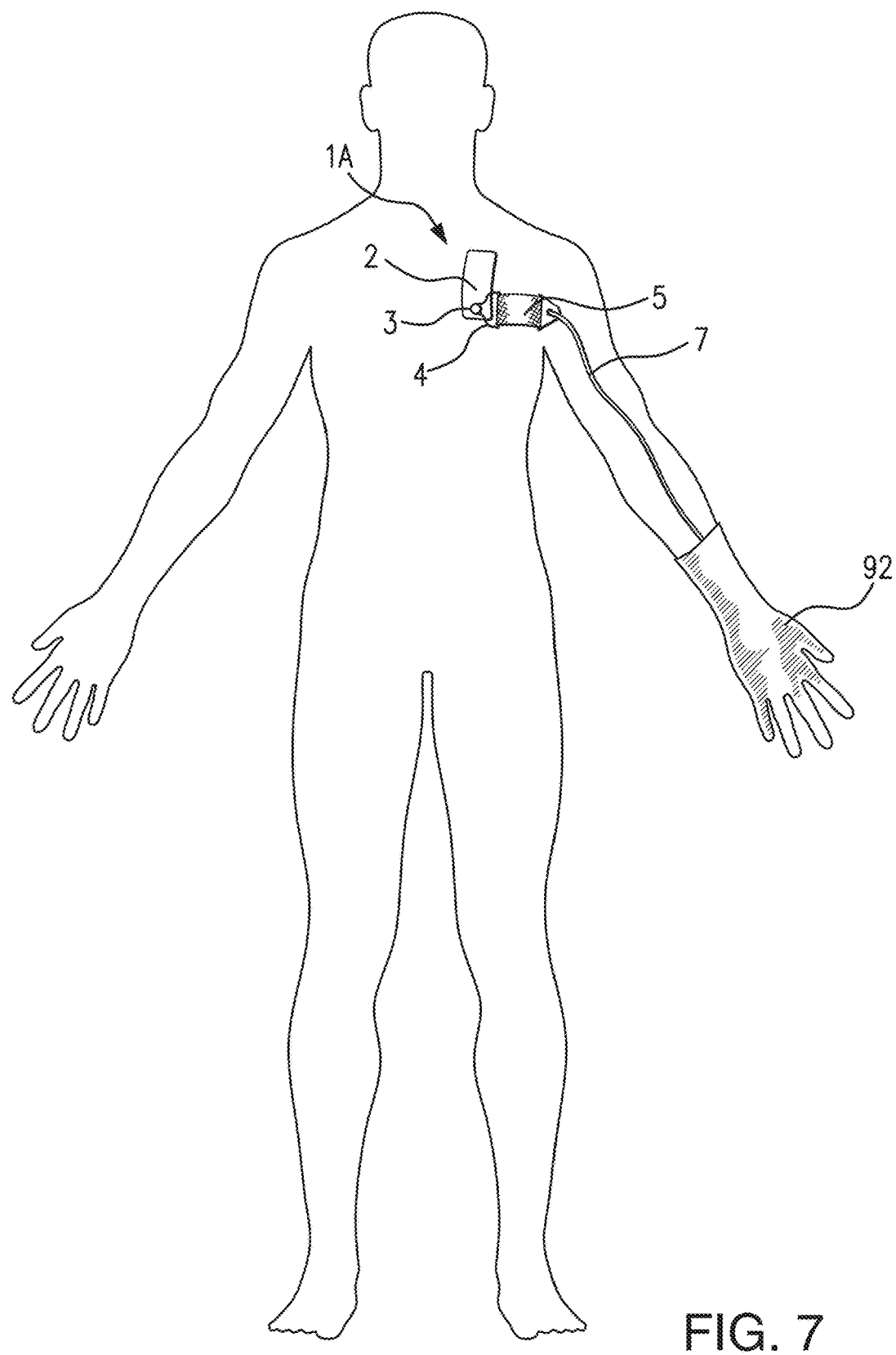
FIG. 7 is a posterior schematic view of a wearer of a below elbow prosthetic arm used in conjunction with an exemplary anchoring system according to the disclosed subject matter.

When the anchoring system includes two clasp-engaging members, as illustrated in FIG. 6a, the anchoring system can be adhered to the wearer such that one clasp-engaging member 3 is aligned substantially horizontally with the axilla and the second clasp-engaging member 3' is positioned substantially vertically above the first clasp-engaging member. In this manner, one clasp-engaging member can be coupled with a cable for manual operation of the prosthetic or orthotic device, and the other clasp-engaging member can be coupled with a cable to support the prosthetic or orthotic device or otherwise operates a different feature. It is to be appreciated that although an above elbow prosthesis was depicted in FIG. 6a, other upper limb prosthetic devices and orthotic devices can be used with the anchoring system disclosed herein.

Figure 6B:
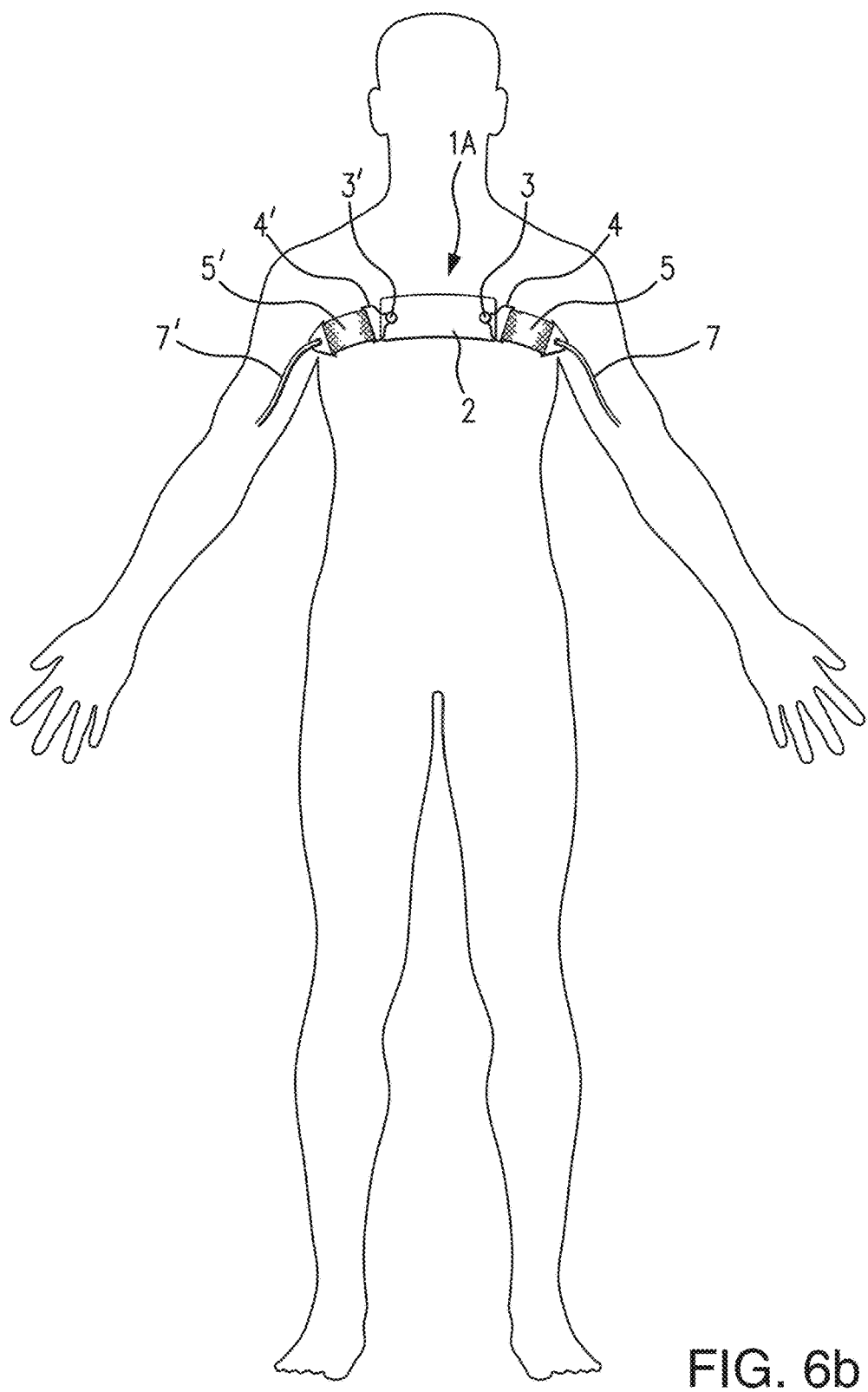
FIG. 6b is a posterior schematic view of a wearer of an above elbow prosthetic arm used in conjunction with an exemplary anchoring system having two clasp-engaging members according to the disclosed subject matter.
Figure 6C:
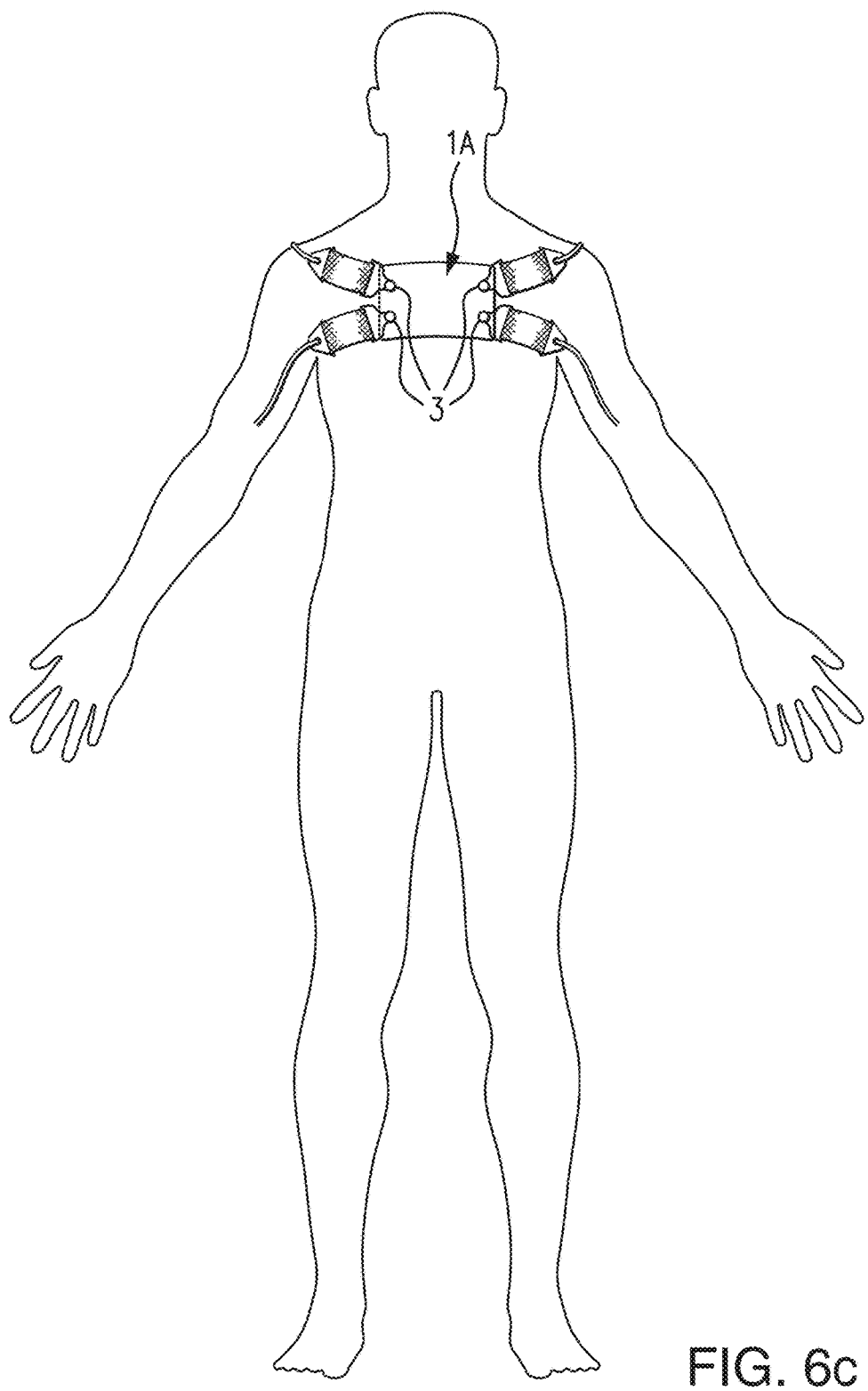
FIG. 6c is a posterior schematic view of a wearer of an above elbow prosthetic arm used in conjunction with an exemplary anchoring system having four clasp-engaging members according to the disclosed subject matter.

Alternatively, and as illustrated by FIG. 6b, the anchoring system 1A having two clasp engaging members (3 and 3') can be placed horizontally across the spine, between the scapulae at the latitude of the axillae. A cable 7 of a prosthetic or orthotic device (not shown) can be coupled with a clasp-engaging member 3 via a clasp 4 and a linker 5. Additionally, a cable 7' of another prosthetic or orthotic device (not shown) worn on the other side of the wearer can be coupled with the other clasp-engaging member 3' via a clasp 4' and a linker 5'. Such a configuration can be useful for wearers having bilateral trans-radial deficiency. Further, by using an anchoring system having four clasp-engaging members, as illustrated in FIG. 6c, bilateral trans-humeral components can be attached and/or activated. These configurations allow access to the anatomical changes provided by the scapular movements of the wearer, which can be isolated from each other. As such, one shoulder can perform a different action from the other.

Figure 8:
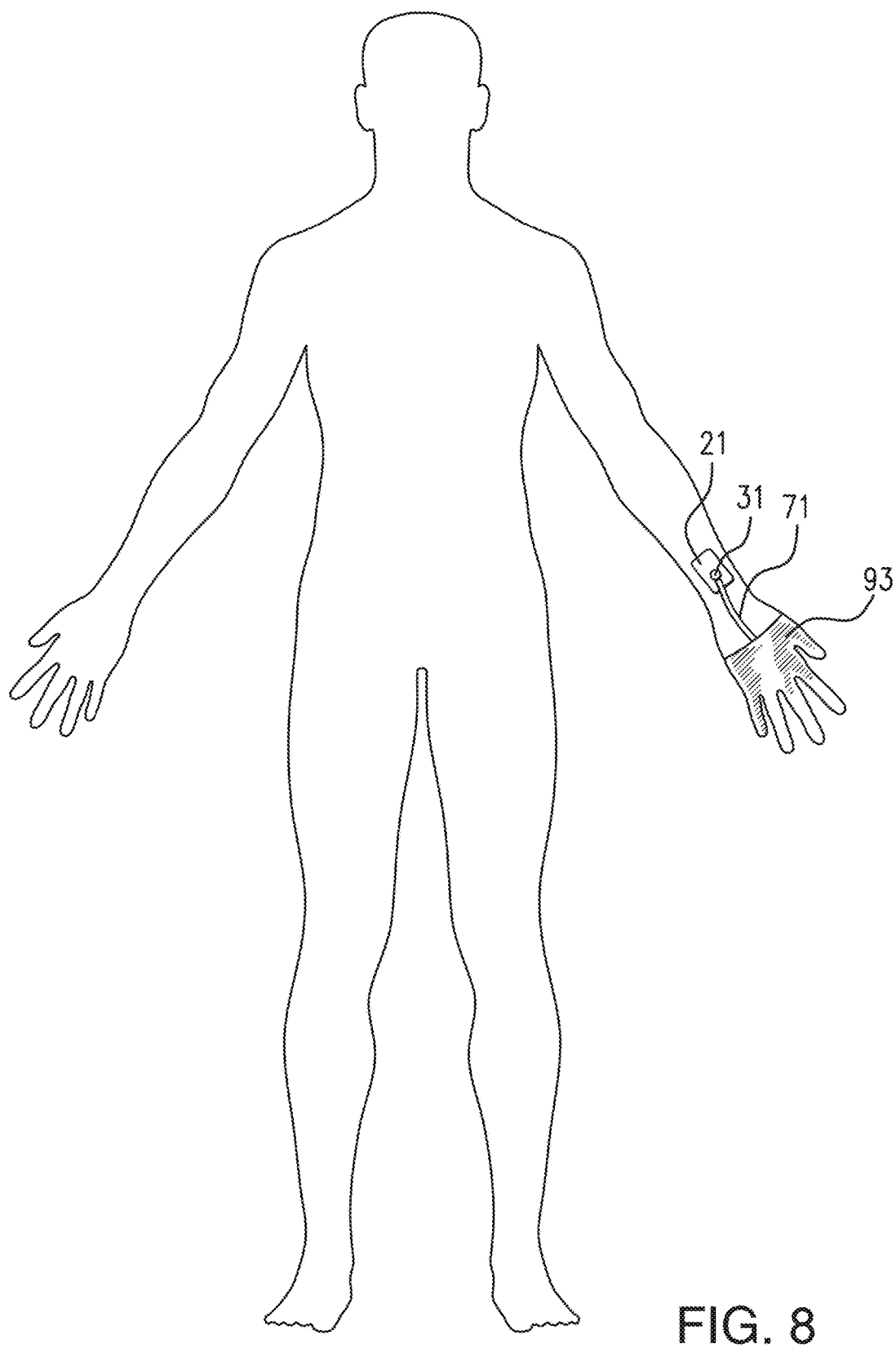
FIG. 8 is a posterior schematic view of a wearer of a prosthetic partial hand used in conjunction with an exemplary anchoring system according to the disclosed subject matter.
Figure 9:
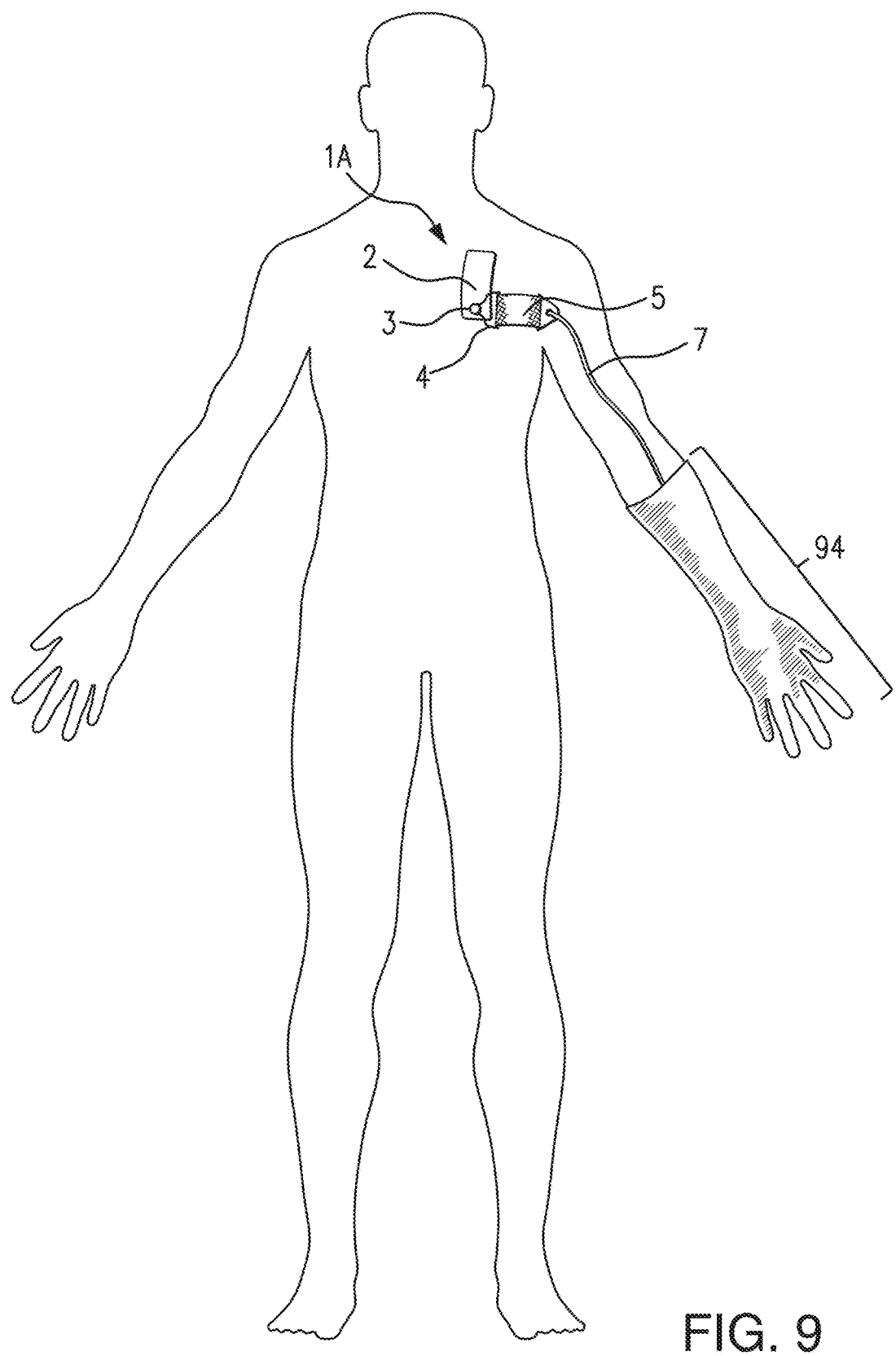
FIG. 9 is a posterior schematic view of a wearer of an upper limb orthotic device used in conjunction with an exemplary anchoring system according to the disclosed subject matter.

In an alternative configuration, such as with a partial hand orthosis or a dynamic hand, the anchoring system can be adhered to the forearm (or upper arm) of the wearer, as illustrated in FIG. 8. In this manner, the base 21 and the clasp-engaging member 31 can be suitably sized to fit on the wearer's forearm. If the prosthetic hand 93 includes multiple digits, each having an activation cable, a plurality of such anchors can be used, each coupled to a cable corresponding to an individual digit, or a single anchor can be provided with multiple clasp-engaging members each coupled to a cable corresponding to an individual digit.

Figure 10:
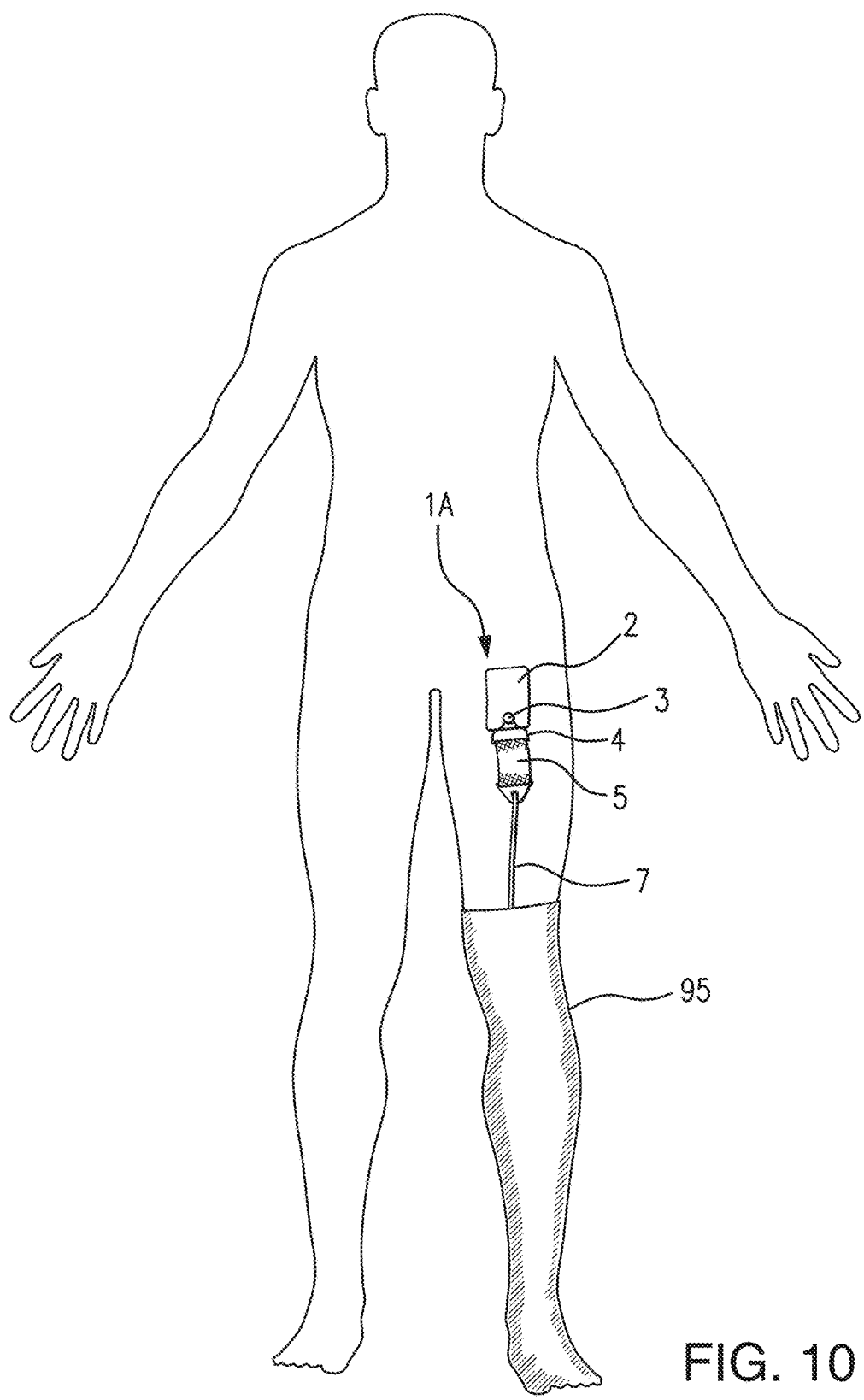
FIG. 10 is a posterior schematic view of a wearer of a prosthetic leg used in conjunction with an exemplary anchoring system according to the disclosed subject matter.
Figure 11:
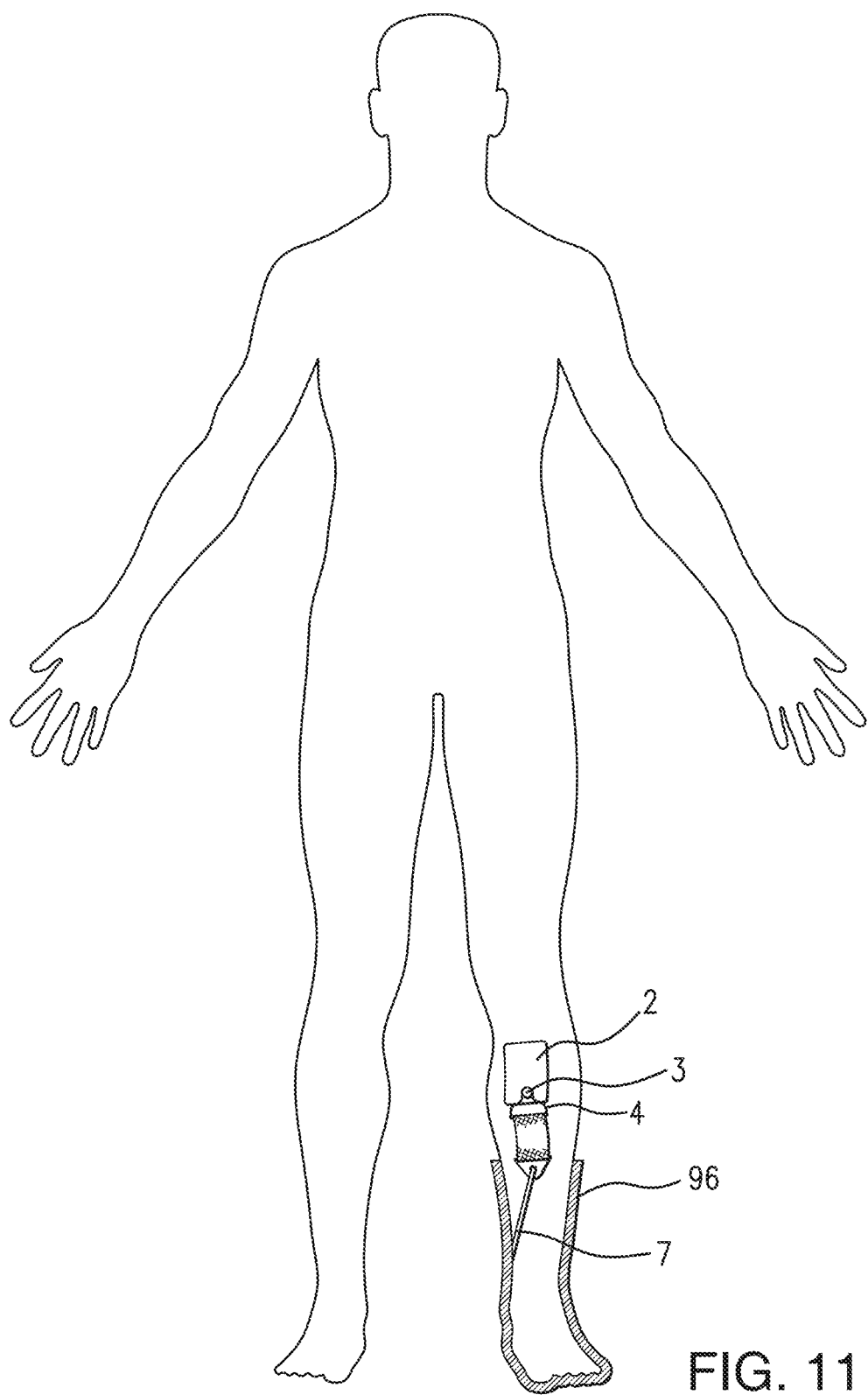
FIG. 11 is an anterior schematic view of a wearer of a lower limb orthotic device used in conjunction with an exemplary anchoring system according to the disclosed subject matter.

As previously noted, the anchoring system can also be used with lower limb prostheses and orthotic devices. For example, the system can be used with a cable-activated prosthetic leg 95 such as a below knee prosthesis or above knee prosthesis, as illustrated in FIG. 10, or a dynamic leg splint such as a knee splint, or an ankle foot orthosis 96 as illustrated in FIG. 11. As shown in FIGS. 10-11, for a lower limb prosthetic or orthotic device, the anchoring system 1A can be placed ipsilaterally with respect to the prosthesis or the orthosis. When the prosthetic device is a leg prosthesis, the anchoring system 1A can be adhered, for example, to the patient's iliac crest, as shown in FIG. 10. When the orthotic device is an ankle foot orthosis, such as for treating or correcting foot drop, the anchoring system can be placed on the anterior tibialis of the wearer.

For purpose of illustration and not limitation, Table 1 below summarizes various prosthetic and orthotic devices that can be used with the anchoring system of the disclosed subject matter, and the corresponding suitable locations the anchoring system can be adhered on the body of the wearer.

TABLE 1

| Prosthetic or Orthotic Devices | | | Placement of Anchoring System on the Wearer |
|---|---|---|---|
| Upper Limb | Above Elbow | Prosthesis | Back (ipsilateral, lateral to spine and medial to scapula) |
| | | Orthosis (e.g., dynamic splint) | Back (ipsilateral, lateral to spine and medial to scapula) |
| | Below Elbow | Prosthesis | Back (ipsilateral, lateral to spine and medial to scapula) |
| | | Orthesis (e.g., dynamic splint) | Back (ipsilateral, lateral to spine and medial to scapula) |
| | Hand/Partial Hand | Prosthesis | Back (ipsilateral, lateral to spine and medial to scapula); upper arm, or forearm |
| | | Orthosis (e.g., dynamic hand) | Back (ipsilateral, lateral to spine and medial to scapula); upper arm, or forearm |
| Lower Limb | Above Knee | Prosthesis | iliac crest |
| | | Orthosis | iliac crest |
| | Below Knee | Prosthesis | iliac crest |
| | | Orthosis | anterior tibialis |

The system is suitable for use with any population, child or adult, having a condition (including congenital or acquired) that benefits from the use of a cable-activated and/or supported prosthetic or orthotic device. For example, it can be used in those having a below elbow upper limb deficiency, spinal cord injury, brachial plexus palsy, cerebral palsy with hemiplegia, head trauma, or hand trauma, among many others.

The disclosed subject matter will be further described in the following examples, which do not limit the scope of the invention defined by the claims.

EXAMPLE 1

Construction of an Exemplary Fastener and Use Thereof

FIGS. 3A-3G illustrate the assembly of an exemplary fastener. Assembly in this instance requires a perforated thermoplastic material, such as AQUAPLAST-T™, a bachelor button (e.g., a Dritz® bachelor button) fastened through and held approximately in the center by the perforated thermoplastic material (see FIG. 3A). A double sided tape, such as toupee tape, was cut to roughly the size of the perforated thermoplastic material (see FIGS. 3B-3D). The double sided tape was trimmed from the perforated thermoplastic material (see FIG. 3E). The backing was then removed from the double sided tape to yield a fastener prepared for use (see FIGS. 3F-3G).

Figure 4A:
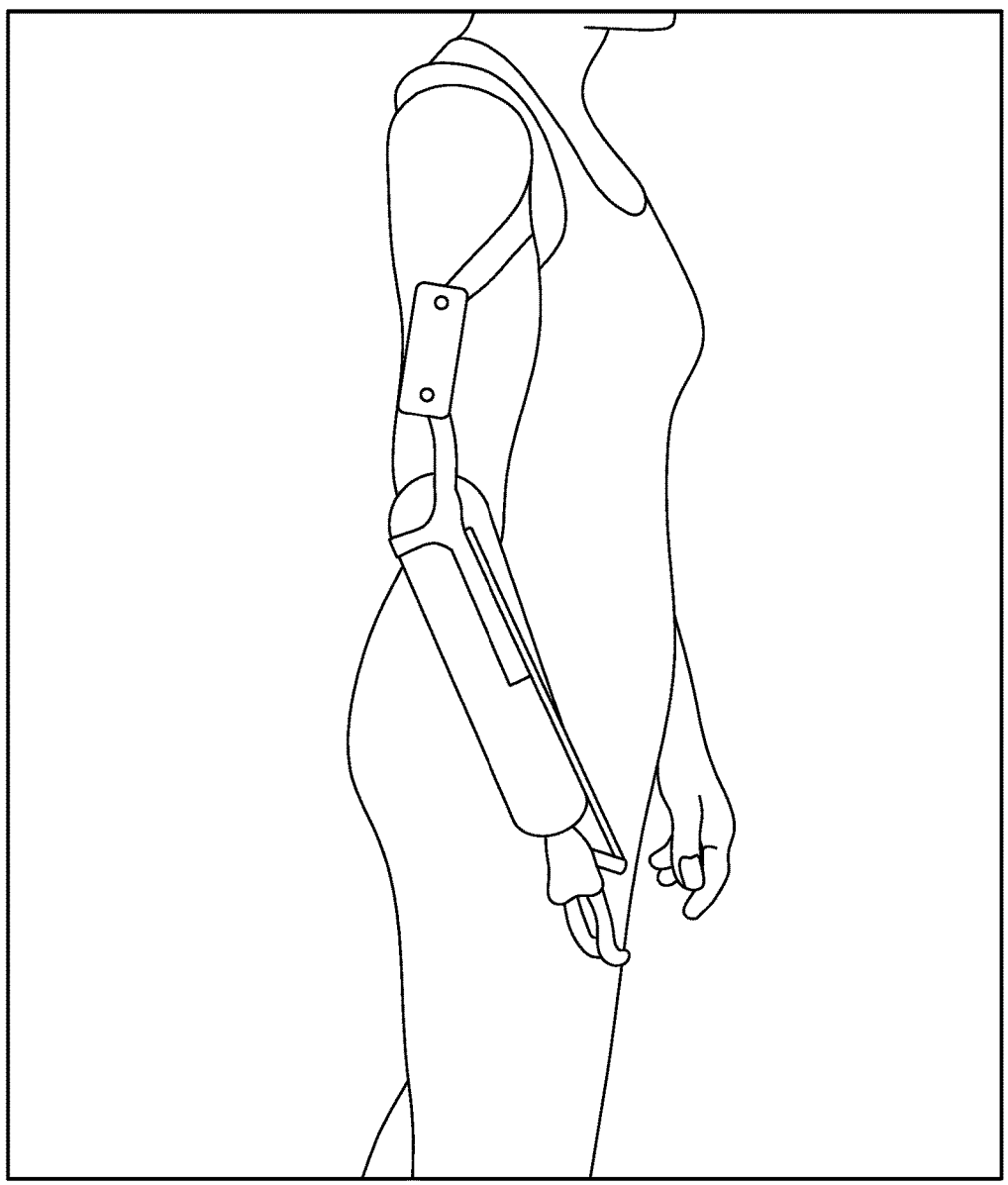
FIGS. 4A-4D illustrate the use of a "Figure of 8" harness system by a wearer of a prosthesis.
Figure 4B:
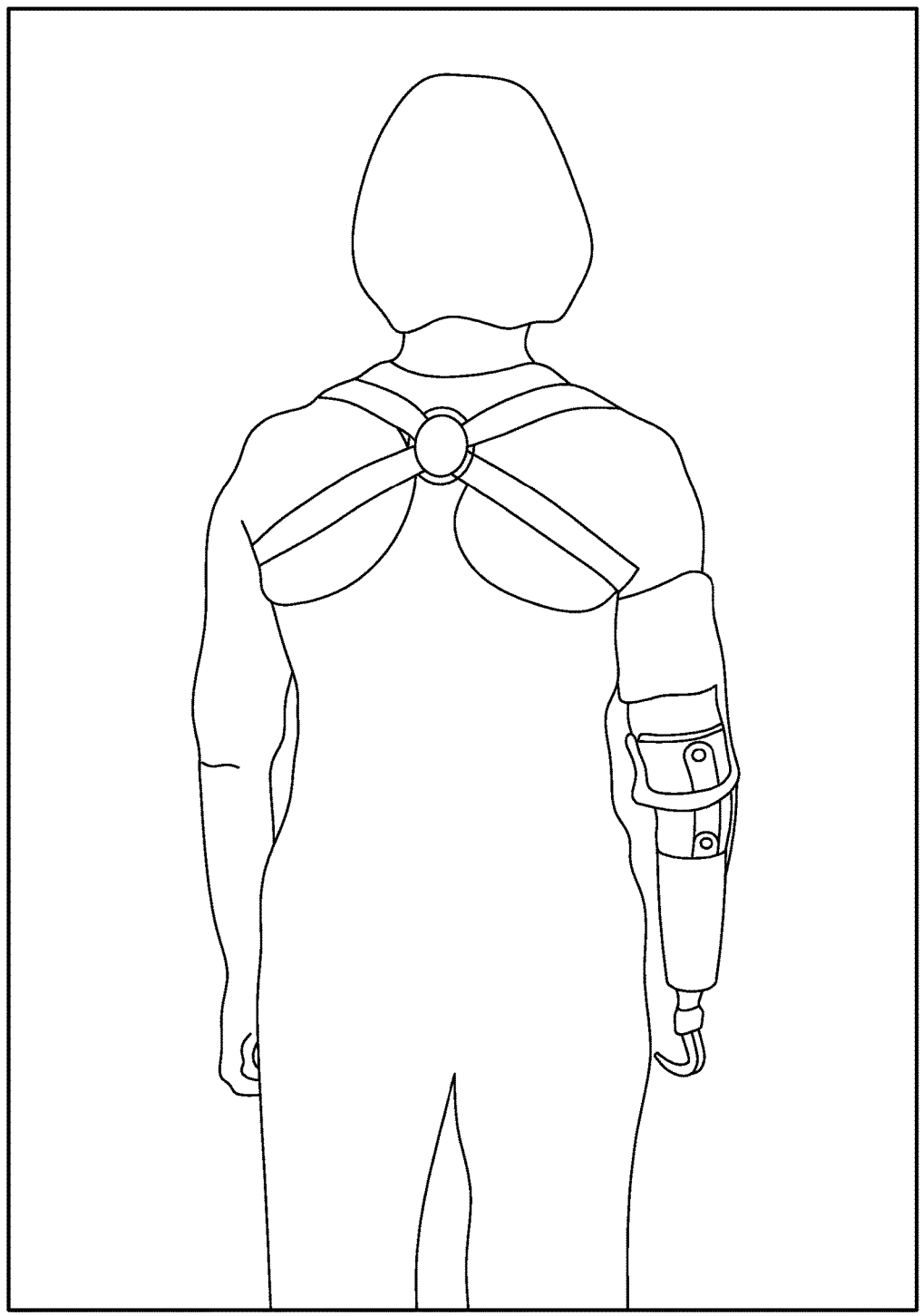
Figure 4C:
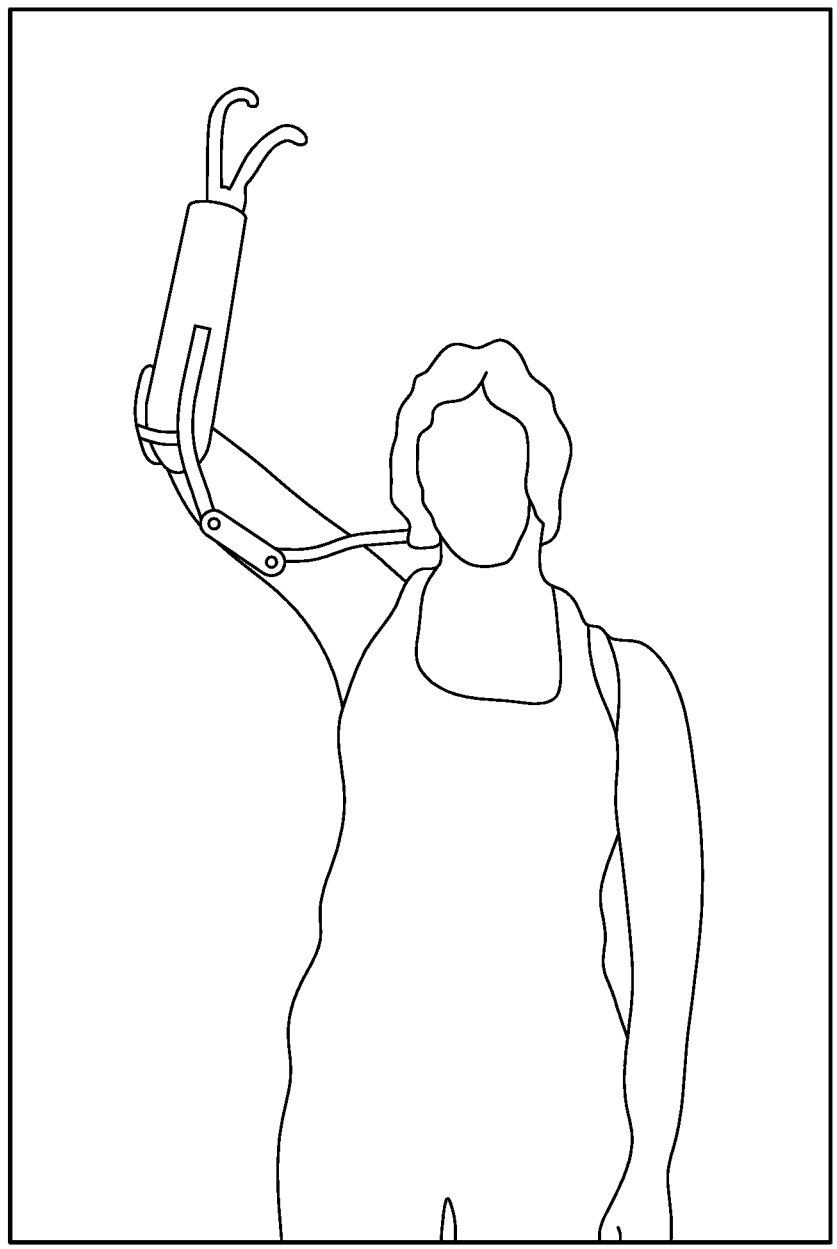
Figure 4D:
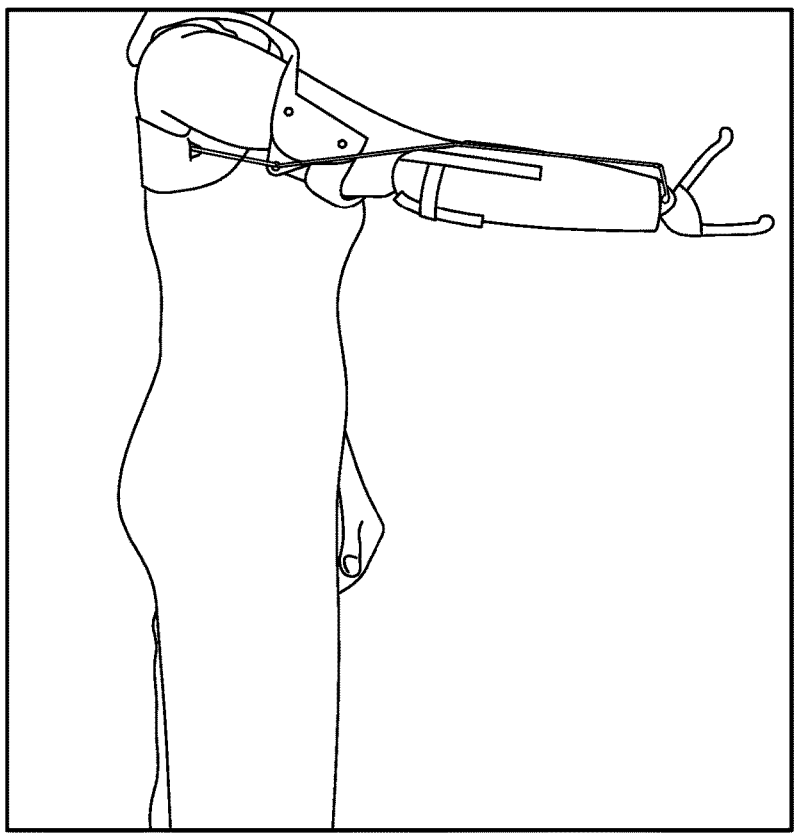

For the purposes of contrasting the embodiment demonstrated in the present Example with prior art systems, FIGS. 4A-4D are presented. These figures illustrate the use of a prior art system—a so-called "Figure of 8" harness system. FIG. 4A is a side view of a wearer of the harness system. FIG. 4B is a back view of a wearer of the harness system. FIG. 4C is a frontal view of a wearer of the harness system, with arm and prosthesis extended above the head. Note how one of the harness straps inconveniently lifts off of and above the right shoulder of the wearer. FIG. 4D is a side view of the wearer with arm extended and prehensile hook in open position.

Figure 5A:
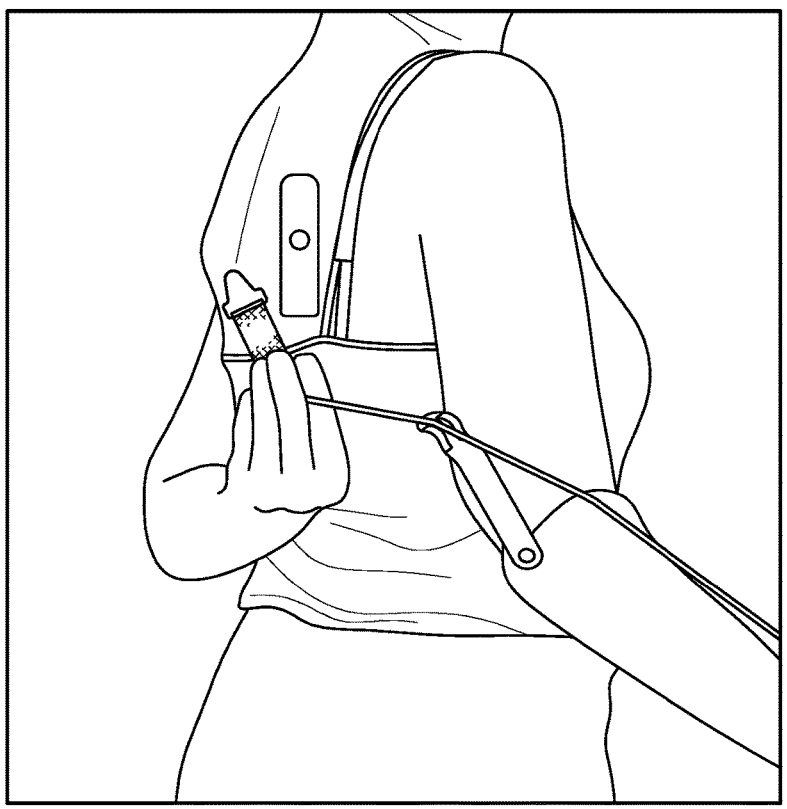
FIGS. 5A-5C illustrate the use of an exemplary anchoring system by a wearer of a prosthesis.
Figure 5B:
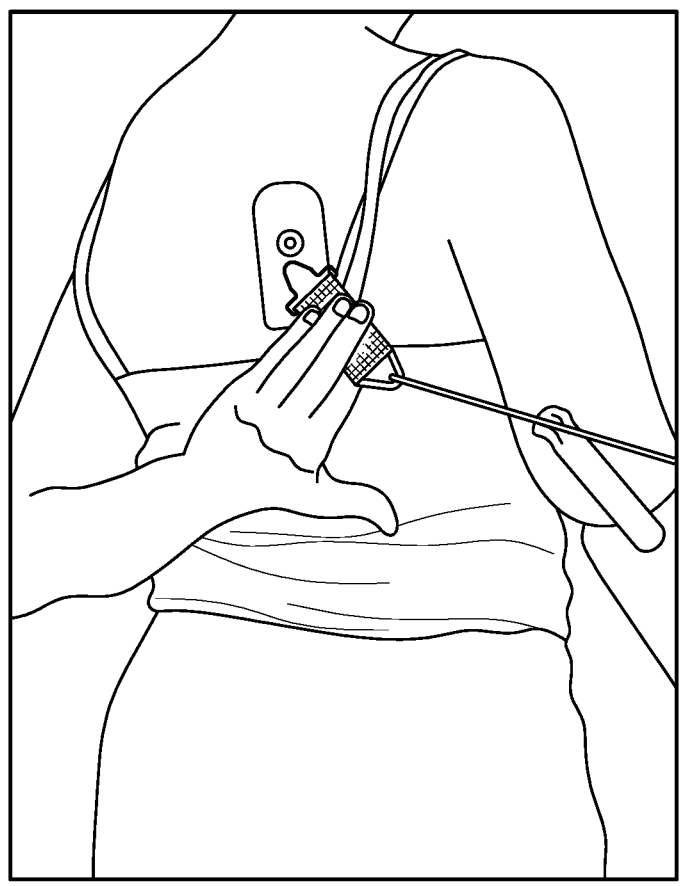
Figure 5C:
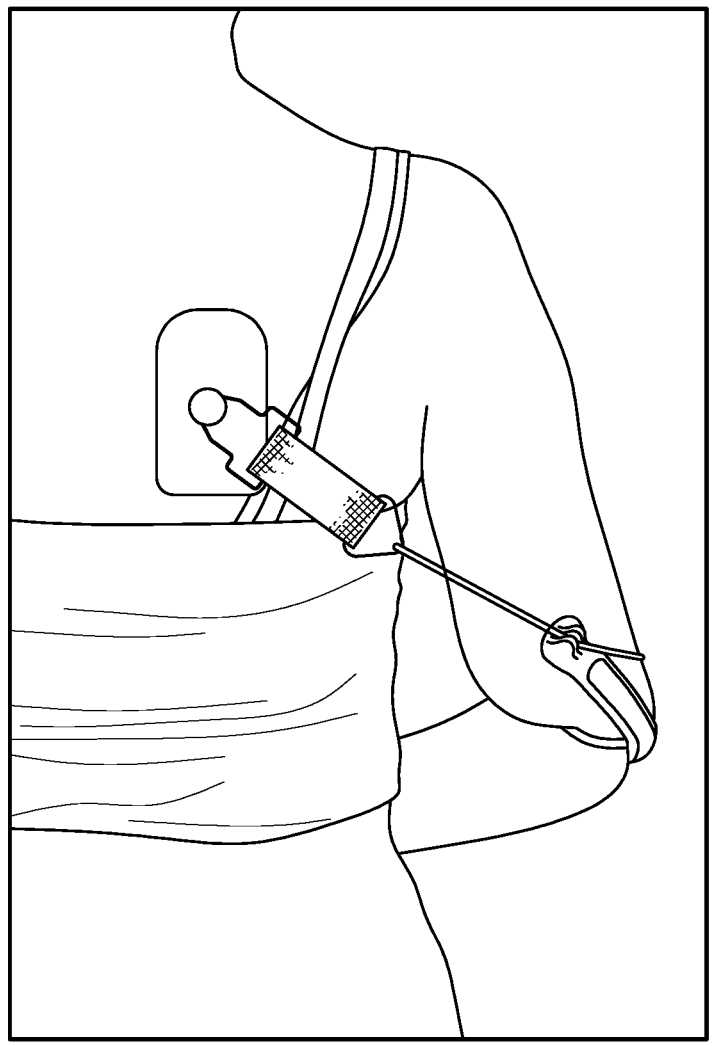

FIGS. 5A-5C illustrate the use of an exemplary anchoring system prepared in part in a procedure similar to that outlined above in FIGS. 3A-3G. Specifically, FIGS. 5A-5C illustrate assembly of a prosthetic system of the disclosed subject matter on a wearer. FIGS. 5A-5C are side view of a wearer with an elbow forearm prosthesis with a modified Muenster socket and a prehensile hook. The fastener was affixed to the wearer's skin just medial to the scapula and slightly above the level of the axilla (see FIG. 5A). The wearer with his/her opposite hand, grasped the clasp and/or linker attached to the activation cable and engaged (e.g., hooked) the clasp with the clasp-engaging member (FIG. 5B). Upon engagement, the device was fully assembled and activated (FIG. 5C).

While the present application is described herein in terms of certain exemplary embodiments, those skilled in the art will recognize that various modifications and improvements can be made to the disclosed subject matter without departing from the scope thereof. Thus, it is intended that the present application include modifications and improvements that are within the scope of the appended claims. Moreover, although individual features of one embodiment of the application may be discussed herein and not in other embodiments, it should be apparent that individual features of one embodiment can be combined with one or more features of another embodiment or features from a plurality of embodiments.

In addition to the specific embodiments claimed below, the application is also directed to other embodiments having any other possible combination of the dependent features claimed below and those claimed above. As such, the particular features presented in the dependent claims and disclosed above can be combined with each other in other manners within the scope of the application such that the application should be recognized as also specifically directed to other embodiments having any other combinations. Thus, the foregoing description of specific embodiments of the application has been presented for purposes of illustration and description. It is not intended to be exhaustive or to limit the application to those embodiments disclosed.

What is claimed is:

1. An anchoring system comprising:
   (i) a fastener including a substantially planar base, and a first clasp-engaging member protruding perpendicularly from the portion of the base to define an axis of rotation and having an outwardly-extending flange, the fastener further including an adhesive suitable to secure the base directly to the skin of a wearer, and
   (ii) a clasp having a first end configured to engage and rotate about the axis of rotation defined by the first clasp-engaging member and a second end configured to engage a cable of a prosthetic or orthotic device, wherein the fastener and clasp are configured to facilitate manual operation of the cable of the prosthetic or orthotic device when the clasp is engaged with the fastener, the adhesive having a sufficient strength to remain adhered to the skin during manual operation of the prosthetic or orthotic device.

2. The anchoring system of claim 1, wherein the base is made from a material selected from the group consisting of a fabric, a thermoplastic material, a metal, or a mixture thereof.

3. The anchoring system of claim 1, wherein the base includes a flat member and the adhesive is disposed on a surface of the flat member opposite the first clasp-engaging member.

4. The anchoring system of claim 1, wherein the first clasp-engaging member is detachably connected to the base.

5. The anchoring system of claim 1, wherein the adhesive is selected from the group consisting of a medical glue, a medical tape, and a double sided tape.

6. The anchoring system of claim 1, wherein the first end of the clasp includes a loop or a hook.

7. The anchoring system of claim 1, wherein the cable is an activation cable for the prosthetic or orthotic device.

8. The anchoring system of claim 1, wherein the cable is a supporting cable for the prosthetic or orthotic device.

9. The anchoring system of claim 1, further comprising a linker coupled to the clasp and configured to couple to the cable of the prosthetic or orthotic device.

10. The anchoring system of claim 1, wherein the fastener is configured to be placed in an ipsilateral configuration with respect to the prosthetic or orthotic device.

11. The anchoring system of 1, wherein the prosthetic device or orthotic device is an upper limp prosthesis.

12. The anchoring system of claim 11, wherein the upper limp prosthesis is selected form the group consisting of an above elbow prosthesis, a below elbow prosthesis, a hand prosthesis, and a partial hand prosthesis.

13. The anchoring system of claim 11, wherein the fastener is configured to be placed between a scapula and a spine, and medial to the scapula of the wearer.

14. The anchoring system of claim 11, wherein the upper limb prosthesis is a hand prosthesis or a partial hand prosthesis, and the fastener is configured to be placed on a forearm of the wearer.

15. The anchoring system of claim 11, wherein the fastener further includes (a) a second clasp-engaging member spaced apart from the first clasp-engaging member, and (b) a second clasp having a first end configured to engage and rotate about the second clasp-engaging member.

16. The anchoring system of claim 15, wherein the fastener is configured to be adhered to the back of the wearer such that the first clasp-engaging member is horizontally aligned substantially with the axilla and the second clasp-engaging member is positioned substantially vertically above the first clasp-engaging member.

17. The anchoring system of claim 15, wherein the fastener is configured to be adhered to the back of the wearer between the scapulae of the wearer such that each of the first clasp-engaging member and the second clasp-engaging member is horizontally aligned substantially with the axillae.

18. The anchoring system of claim 1, wherein the prosthetic or orthotic device is an upper limb orthotic device.

19. The anchoring system of claim 18, wherein the upper limb orthotic device is selected from the group consisting of a dynamic hand, a dynamic forearm, and a dynamic elbow.

20. The anchoring system of claim 1, wherein the prosthetic or orthotic device is a lower limb prosthesis.

21. The anchoring system of claim 20, wherein the fastener is configured to be adhered to an iliac crest of the wearer.

22. The anchoring system of claim 20, wherein the fastener is configured to be adhered to an anterior tibialis.

23. The anchoring system of claim 1, wherein the prosthetic or orthotic device is a lower limb orthotic device.

24. The anchoring system of claim 23, wherein the lower limb orthotic device is hinged ankle foot orthosis.

* * * * *